United States Patent [19]

Chalifoux

[11] Patent Number: 5,316,478
[45] Date of Patent: May 31, 1994

[54] DENTAL POST WITH CUTTING SURFACES

[75] Inventor: Paul R. Chalifoux, Wellesley, Mass.

[73] Assignee: Wellesley Research Associates, Inc., Wellesley, Mass.

[21] Appl. No.: 908,366

[22] Filed: Jul. 6, 1992

Related U.S. Application Data

[63] Continuation-in-part of Ser. No. 739,670, Aug. 2, 1991.

[51] Int. Cl.$^5$ ............................................. A61C 5/08
[52] U.S. Cl. .................................. 433/221; 433/165; 433/220
[58] Field of Search ................ 433/76, 165, 166, 220, 433/221

[56] References Cited

U.S. PATENT DOCUMENTS

| | | | |
|---|---|---|---|
| 1,140,539 | 5/1915 | Skinner | 433/220 |
| 1,200,921 | 10/1916 | Chester | 433/165 |
| 1,517,500 | 12/1924 | Fredericks | 433/221 |
| 2,655,724 | 10/1953 | Brooks | 433/21 |
| 5,066,230 | 11/1991 | Weissman | 433/221 |
| 5,094,618 | 3/1992 | Sullivan | 433/221 |

FOREIGN PATENT DOCUMENTS 844341  7/1952  Fed. Rep. of Germany ...... 433/220

Primary Examiner—John J. Wilson
Attorney, Agent, or Firm—Paul J. Cook

[57] ABSTRACT

A dental post is provided comprising a bottom section with cutting projections and a stem section. The cutting projections cut paths into the root canal walls to provide retention and anti rotation. A disk may be included which has projections on the bottom which cut pathways into the top of the root for optimal post support and root fracture resistance.

21 Claims, 5 Drawing Sheets

DENTAL POST WITH CUTTING SURFACES

This application is a continuation-in-part of copending application Ser. No. 07/739,670 filed Aug. 2, 1991.

BACKGROUND OF THE INVENTION

This invention relates to a dental post construction which can be inserted into a tooth stub and which is utilized to improve retention of a dental restoration built onto the tooth stub.

It is present dental procedure to form a dental prosthetic structure onto a tooth stub for replacement of missing dentition. In this procedure, a tooth stub is initially prepared by removing the diseased or damaged top portion of a tooth to form a tooth stub. A base is formed by drilling into the root canal portion of the tooth stub to form a space into which a dental post can be inserted. Presently available dental post include grooves on their surface designed to improve retention of the post within the tooth stub. Dental cement is employed in the bore in conjunction with the dental post to secure the post in the tooth stub. A portion of the post extends above the tooth stub upper surface so that a dental prosthesis formed on the tooth stub can be retained. Presently, the implantation of a dental post relies either upon the adherent strength of an adhesive or on lateral stress forces between the dental post and the canal wall of screw type posts.

Preformed posts are posts which are premade to specific dimensions with matching burs having cutting surfaces. The burs have a matching diameter to the post and prepare the root to accept a post. A post is then tried in the root and cut to the appropriate length. Cement is spun into the canal with a device referred to as a lenticulo spiral, placed directly with a syringe and/or placed directly on the post. The post is placed in the canal and held in position until excess cement extrudes and the cement hardens. Most preformed posts require placing filling material around the top of the post to transfer strength from the post to the crown. This procedure is referred to as the core build up or post and core procedure.

There are many problems which are encountered when utilizing preformed posts. These include:

An inaccurate fit develops with present bur technology.

Potential for perforation of the root is great with present burs.

There is inadequate resistance to rotational forces on the post.

Root fracture caused by lateral stresses occurs.

There is weak transfer of strength from the post to the crown positioned on the post.

An accurately drilled hole results in good proximity of the post to the canal walls with a thin cement layer to provide greater success in properly positioning the post. The hole is inaccurate if tipping or vibrating of the bur occurs during root preparation as occurs with present drilling systems. This adds to the failure rate of preformed post systems. Drilling a straight hole for a straight post in a curved canal or drilling a hole which does not align with a canal can lead to perforation of a root and loss of a tooth. All posts must resist normal rotational forces which occur during normal or abnormal functions if there is not sufficient tooth structure to provide resistance. In general, preformed posts do not provide good stability against rotational force because they are round and rotate easily when placed in a round hole such as that provided by present bur systems. Presently, to compensate for this, a separate pin may be placed into the tooth, however, screw pins increase the likelihood of root fracture. Some systems try to make posts oval or non-symmetrical at the top but do not supply dependable resistance and retention form. Cement merely provides suction to hold a post in position. The strength of the cement becomes a weak point to the root-post-crown relationship. Constant repeated forces of chewing causes potential breakdown on the tooth-cement-crown interface with subsequent cement wash out and crown post failure. An uneven or excessive amount force can cause root fracture and tooth loss. Screw type posts can exert large lateral stresses which leads to potential root fracture and tooth loss. In addition, forceful placement of cement type posts without proper venting of cement can cause root fracture and tooth loss. Filling material is placed around a preformed post above the root to accept a crown after the post is cemented. The strength and long term stability of this material becomes a weak link in long term success of the crown. In addition, proper design of the post above the root is critical to resist rotation or dislodging of the filling material from the post.

A cast post is inducted for root canalled teeth with no clinical crown (no tooth above the height of the gums) and/or teeth with root canal spaces which are shaped in such a manner that a preformed post can not fit properly. For example, a canal may be narrow at its bottom half and diverge rapidly in the top half or it may be too oval shaped. The preformed post which is of the same diameter throughout can not accommodate these situations. When utilizing a cast post, root preparation is done by drilling to remove undercuts and obtain slight divergence from the bottom upward. The cast post technique takes an impression of a prepared root canal space. In indirect methods, an impression of the root is taken with a dental impression material. In direct methods, an acrylic pattern of the prepared root and the desired shape above the gums is achieved in the mouth. Laboratory procedures which include casting in a lost wax technique are then necessary to construct the cast post. There are many problems which are encountered when utilizing casts posts. The problems include: An increased chance of root fracture. The cast post is expensive. There is an increased possibility of root perforation. The cast post may not provide good resistance to rotational forces.

All posts need to provide venting of cement as a post is placed. A cast post is very precise fitting so it is difficult for cement to vent, lateral forces can fracture the root and/or the post will not be fully seated as excess cement remains in the bottom. In addition, any bubbles or inaccuracies from the casting process can cause a poor fit and root fracture. Cast posts dramatically increases cost as compared to preformed posts because there are laboratory fees and increased time required to treat the patient. For a cast post, an appointment is needed for an impression in addition to an appointment for post placement. The patient cost of a cast post is double the cost of a preformed post. The doctors laboratory cost may be five to ten times the cost to buy a preformed post.

Preparation of a root canal space must be free of any undercuts or removal of a cast post in its plastic or wax phase of construction will be impossible. It is often difficult to attain this as root canals tend to be complex systems of lateral canals, ribbon shapes, multiple canals, etc. Often, excessive drilling is done which removes important tooth structure and leads to a weaker root and increased chance of root fracture or perforation.

It has been proposed in U.S. Pat. Nos. 4,480,997; 4,490,116 and Re 31,948 to utilize a threaded dental post which is introduced into the bore of a tooth stub by being rotated to thread the post into position. The dental post includes a stem portion having a slot extending through the stem thickness and along its length which renders the stem being formed of two legs each having its outside surface threaded. The outside surface of the legs intimately contact the walls of the bore so that the threads on the legs can engage the walls. In addition, a spring-like connection for the two legs is provided so that a radial outward spring force is applied to the legs to force them against the bore walls. These dental posts are undesirable since a rotational force must be applied to the post to position it properly into the bore. This positioning process is undesirable since it is time consuming and causes the patient discomfort. In addition, the possibility exists that the post will be threaded too far into the tooth stub which will result in fracture of the tooth stub. Furthermore, the radially outward forces of the legs on the tooth stub can result in fracture of the tooth stub over time.

U.S. Pat. No. 1,534,409 discloses a two legged post having corrugated surfaces which fit into a root canal having generally parallel walls. This surface design materially reduces the post surface area which contacts the canal walls and thus post retention relies primarily upon cement adhesive strength.

Accordingly, it would be desirable to provide a dental post which can be inserted into the bore of a tooth stub while eliminating the need for sole reliance upon lateral stress forces with the canal wall or upon the adhesive strength of an adhesive. In addition, it would be desirable to provide a dental post which interacts with indentations in the walls of the bore by mechanical interaction in order to retain the post in the bore while minimizing or eliminating forces on the walls exerted by the post. In addition, it would be desirable to provide a system for forming a mating bore in a tooth stub for such a dental post by utilizing the dental post as the bur for forming the means for mechanical interaction between the post and the tooth stub and for properly positioning the post manually within the bore. Furthermore, it would be desirable to provide a system for utilizing such a dental post which facilitates the placement of a core and a crown.

SUMMARY OF THE INVENTION

This invention provides a dental post having a stem section and a bottom section. The stem section has areas which match to the inside surfaces of holders, handles or pliers such as flat surfaces. The bottom section has a series of cutting projections which may be of any shape including hexagonal, rectangular, pointed, oval, round etc. Each projection is provided with a material such as diamonds, stainless steel, carbide, titanium or other material of hardness greater than tooth structure, which permits cutting into the wall of the tooth bore by rotating or oscillating the dental post. The post can have, though may not require, venting grooves for cement to vent when placement occurs and allow collection of debris from filing tooth structure. There may also be non-cutting areas along the bottom section of the post which provide guidance for direction during the drilling process.

The bore of the tooth stub is roughly drilled to the approximate shape with customary gates gliddens and peeso reamers resulting in a hole very close to the exact size desired. The post is placed into the bore and held on the stem with any convenient tool such as holders, pliers, or handle or the like. Rotation or oscillation with slight downward pressure will allow the post to drill its own hole resulting in a perfect fit. Optionally, if cement was not placed, the post is removed and debris cleaned. Cement is placed in the bore or on the post. The post is placed fully back down into the bore. It is again oscillated moving it downward several millimeters until it is in final position. Rotation back and forth of less then a quarter turn will produce horizontal slots and relieve any lateral forces. In cases where rotational forces will require resistance the final movement may be random up and down and back and forth. The holders release the post and reduction of length is done if necessary.

This invention also provides a post having a disk at the top of the post which is positioned on the top of a tooth. The bottom and sides of the disk also can have projections which cut into the top surface of a root stub. The projections which extend in a downward direction to assist in retaining the root together and in preventing root fracture, a common problem with posts. The disk also provides for an exact fit of the top of the post to the root stub.

DESCRIPTION OF SPECIFIC EMBODIMENTS

Figure 5:
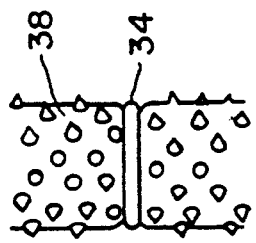
FIG. 5 is a close up side view of an alternative non cutting area of the post if FIG. 4.

The dental post of this invention includes a means for locking it into the walls of a tooth bore without the requirement of maintaining the post under pressure, self-induced or otherwise, against the bore walls. The dental post includes a stem having an extension to be held by a tool such as a handle, holders or pliers and may be of any shape including triangular, rectangular, square, oval, etc. A bottom section of the post has cutting areas which are formed by extensions beyond the core of the post or by removal of material into the core of the post resulting in areas which appear to be extensions. The number of extensions per bottom section may be as few as one or very dense and include hundreds of extensions. The extensions may measure from microns up to about two millimeters. Rotation and oscillation of the post with combined downward pressure results in the post extensions removing tooth structure and forming a path cut by the post extensions. The previous root canal process and canal shaping with gates gliddens and peeso reamers renders the hole approximating the final diameter and equal to the diameter of the shaft of the post so that the post extensions require removal of very little tooth structure. The extensions form a tortuous cut path in the dentin of the tooth bore which makes it impossible for the extensions to follow these paths back out of the canal. Removal of the post would require cutting new paths by the extensions on the way out of the canal as it would be impossible to follow the tortuous path cut during placement. Present helical systems can easily follow the same path out of the canal and therefore come loose easily when rotational force is applied. The post can be used with or without cement to hold it or combined with common bonding procedures. The bottom section of the post can have of any cross sectional shape such as triangular, square, rectangular, oval, etc.

In an alternate form, the extensions completely cover the bottom section of the post such that the post can cut its own path for the shaft and extensions into the tooth stub bore forming an exact fit of the post to the walls of the bore. The post is rotated and inserted slowly by hand rotation to avoid extensive root reduction and an inaccurate fit as would occur with rotation by a drill. Extensions during the cutting of root structure and placement form a rough surface on the bore surface which further aids cement/root retention as cement flows into the resulting grooves. Final placement of the post results with extensions in contact with root structure and therefore mechanical retention by post to root contact with no lateral stress.

In an alternative form, the projections may be designed so placement is possible but removal is impossible. For example, projections may have some surfaces which are rough and cutting and other surfaces which are non cutting. All the sides except the top surface may be cutting, such that when the post is being placed the bottom and side surfaces cut a path for placement of the post, however, the top surface is flat and non cutting such that a force pulling out the post would be resisted by the flat surface. In another version the projection may be pointing up such that the point digs in when removal is attempted.

In an alternative form, the bottom section is completely covered with cutting extensions but there are non cutting areas on the shaft which guide the path of the post to avoid tipping during placement. The non cutting areas may be three hundred and sixty degrees around the bottom section of any shape or interspersed thoughout at one or multiple locations on the shaft. The non cutting areas contact the side of the tooth stub bore and stop the post from tipping and forming an inexact fit.

In an alternative form, the end of the bottom section is non cutting so as to guide the bur down the bore and not allow the bottom tip of the post to drill into the side of the bore. A non cutting tip will prevent perforation of the tooth when drilling is accomplished.

In an alternative form, the stem of the post of this invention has a bend which allows for ease of placement in molar teeth.

In an alternative form, the post can have a weak area of decreased diameter or weaker materials on the stem which is strong enough to allow rotation and yet weak enough to allow breakage when bent back and forth as would occur with notching of the post stem.

In an alternative form, the post has a handle similar to present root canal files, however, this handle can be removed once a post is in place.

In an alternative form, the post can have a through split in the shaft which allows compression of the resulting legs and less lateral force during cutting action of the extensions during placement.

In an alternative form, the post can have a number ov various shapes of the stem including disks, supports, and projections which aid in retention of a core or core material to transfer strength from the post to a prosthesis. A core can include an exact metal fit with and an exterior of composite which allows for ease of alteration and minimum of heat generation.

In an alternate form of this invention a disk is added at the top of the post which is positioned on the top of a tooth. The bottom and sides of the disk can have projections which cut into the top surface of a root stub. The projections which extend in a downward direction can help hold the root together and prevent root fracture. The disk also provides for an exact fit of the top of the post to the root stub. The disk also can have holes for placement of pins to provide further mechanical retention and anti rotational characteristics. The stem and supports can be at various angles in relation to the disk to accommodate teeth out of the normal alignment.

Figure 1:
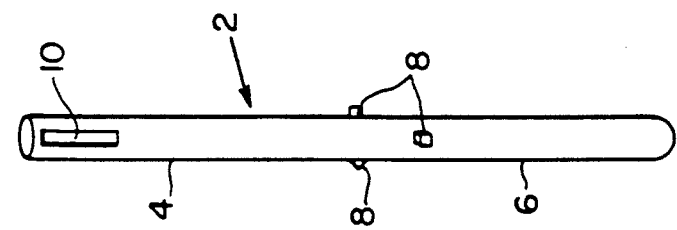
FIG. 1 is an isometric drawing of the post of this invention.

Referring to FIG. 1, the dental post 2 formed from a suitable dental material includes a bottom section 6 and stem section 4. The stem section 4 forms an area 10 which accepts a tool such as holding pliers, a removable handle or holder. The bottom section 6 contains at least one projection 8 of any shape including diamond, triangular, square, rectangular, round, pointed, or the like up to hundreds of projections which are made of material hard enough to cut dentinal tooth structure.

Figure 2:
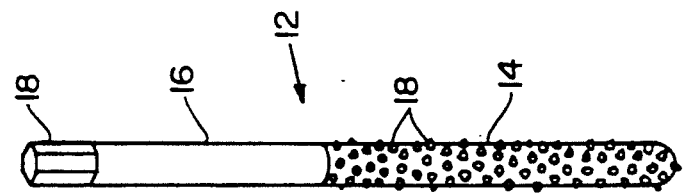
FIG. 2 is an side view of an alternative post of this invention.

Referring to FIG. 2, an alternative dental post of this invention is shown. The post 12 has a bottom section 14 and a stem section 16. The stem section has an area 18 which can accept a tool such as a holder, pliers or handle. The bottom section 14 has hundreds of cutting projections 18 which cut root structure when rotated to place.

Figure 3:
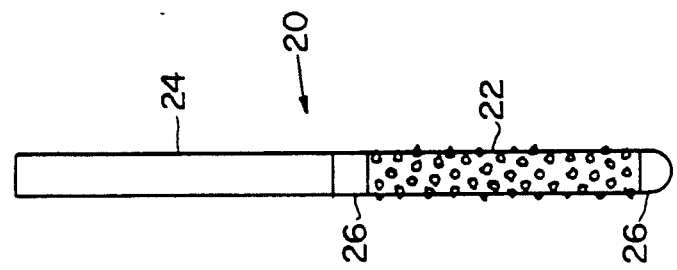
FIG. 3 is side view of an alternative post of this invention.

Referring to FIG. 3, an alternative dental post of this invention is shown. The post 20 has a stem section 24 and a bottom section 22. The bottom section 22 has non cutting areas 26 which provide guidance during cutting root structure such that the post can not drill outside of the root causing perforation.

Figure 4:
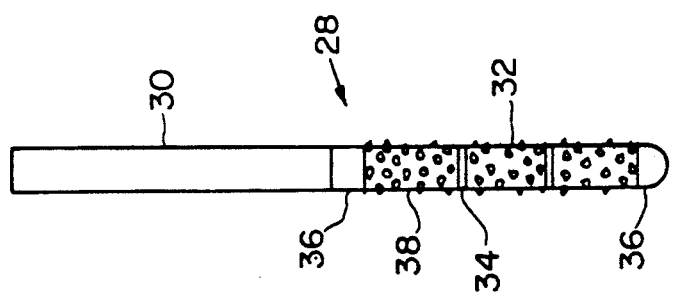
FIG. 4 is a side view of an alternative post of this invention.

Referring to FIG. 4, an alternative dental post of this invention is shown. The post 28 has a stem section 30 and a bottom section 32. The bottom section has non cutting areas 36 and 34 interspersed within cutting areas 38 which provide guidance to maintain a straight path with no tipping of the post.

Referring to FIG. 5, a close up of an alternative non cutting area 34 within the cutting area 38 of the post of FIG. 4 is shown.

Figure 6:
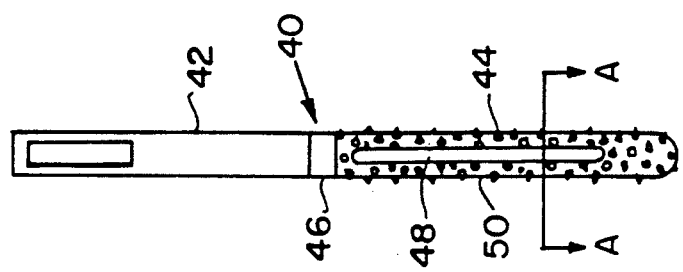
FIG. 6 is a side view of an alternative post of this invention.

Referring to FIG. 6, a side view of an alternative post of this invention is shown. Post 40 has a stem 42 and a bottom section 44. The bottom section 44 has cutting surface 50 and non cutting surface 48 and non cutting surface 46 which prevent tipping of the post during placement. There are multiple areas of non cutting surfaces to prevent tipping in any direction.

Figure 7:
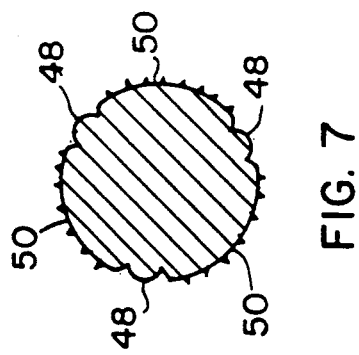
FIG. 7 is a cross section of the post of FIG. 6.

Referring to FIG. 7, a cross section taken along line A—A of the post of FIG. 6 is shown. The post has non cutting surfaces 48 and cutting surfaces 50.

Figure 8:
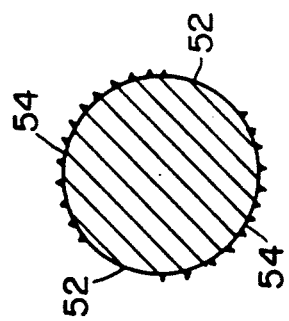
FIG. 8 is an alternative cross section of the post of FIG. 6.

Referring to FIG. 8, an alternative cross section to FIG. 7 is shown with cutting surfaces 54 and non cutting surfaces 52.

Figure 9:
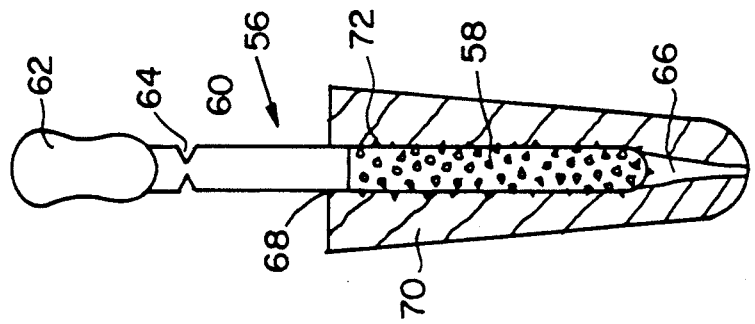
FIG. 9 is a side view of an alternative post of this invention in a root stub.

Referring to FIG. 9, a side view of an alternative post of this invention is shown. Post 56 has a stem section 60 which has a handle 62 attached and break off area 64. Post 56 has a bottom section 58 which is placed in the bore 68 or root stub 70 with extensions 72 cutting into the walls of the root canal space 66.

Figure 10:
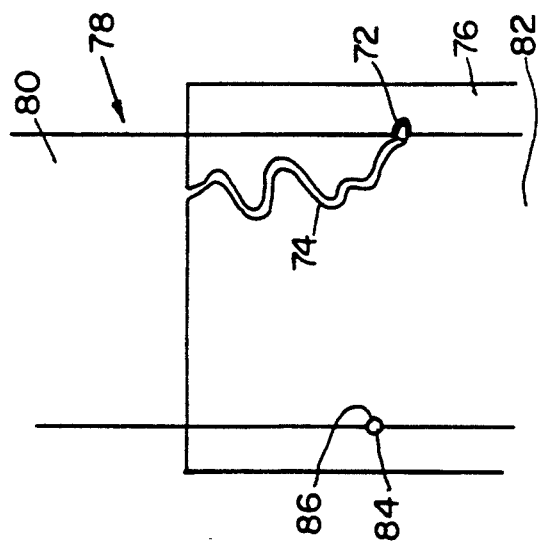
FIG. 10 is an side close up view showing the path cut by a projection of a post of this invention and the projection into root structure.

Referring to FIG. 10, a close up side view of the wall of a tooth stubs root canal space with a post 78 inserted is shown. The extension 72 cuts a path 74 into the root wall 76 during placement. In addition a space in the root 84 will better retain cement and a space 86 in the post will retain excess cement.

Figure 11:
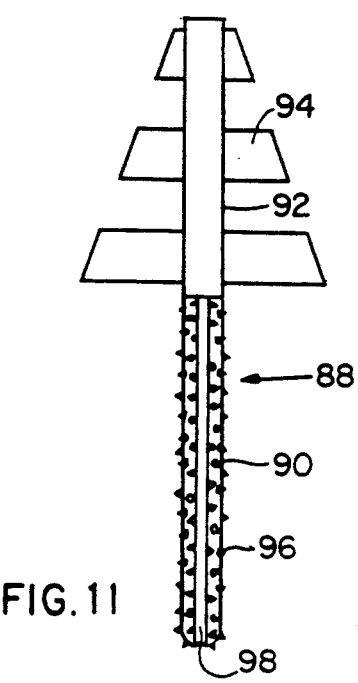
FIG. 11 is a side view of an alternative post of this invention.

Referring to FIG. 11, a side view of an alternative post of this invention. A post 88 with a stem section 92 which has projections 94 which can be of a variety of shapes to hold filling material and a bottom section 90 which has cutting surfaces 96 and cement venting or debris collecting groove 98.

Figure 12:
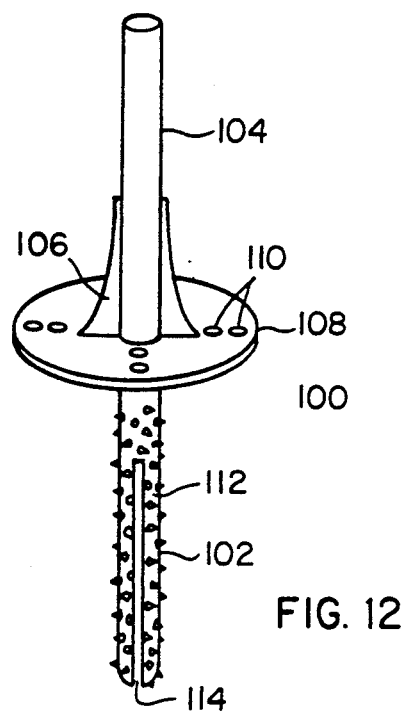
FIG. 12 is an isometric view of an alternative post of this invention.

Referring to FIG. 12, an isometric view of an alternative post of this invention. Post 100 has a stem section 104 and bottom section 102. Stem section 104 has a disk 108, supports 106 and holes 110 for pin placement or bonding material/cement to extrude out. Disk 108 or stem 102 may be angled to accommodate angled teeth. The disk may be of any shape such as round, square, triangular, rectangular, or one sided etc. which may aid in anti rotation if placement of the disk is into root structure instead of just on top of the root stub. The bottom section 102 has a through split 114 and cutting areas 112.

Figure 13:
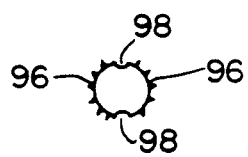
FIG. 13 is a cross section of the post of FIG. 11.

Referring to FIG. 13, a cross section of the bottom section of the post of FIG. 11 is shown. The bottom section has cutting areas 96 and vents 96.

Figure 14:
FIG. 14 is a cross section of the post of FIG. 12.

Referring to FIG. 14, a cross section of the bottom section of the post of FIG. 12 is shown. The bottom section has a through cut 114 and cutting surface 112.

Figure 15:
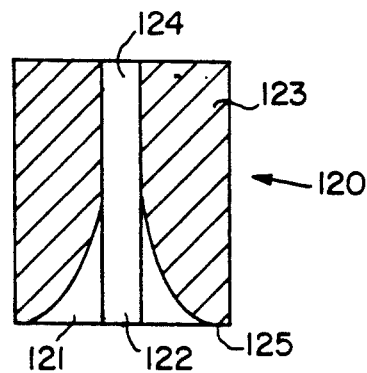
FIG. 15 is a cross section of a core of this invention.

Referring to FIG. 15, a cross section of a core 120 of the invention is shown. Core 120 has a central hole 122 for placement of the stem portion of a post and hole 121 which accepts supports of a post. The core area 123 may be made of metal, composite, resins or other like materials which may transfer strength from the post to a core.

Figure 16:
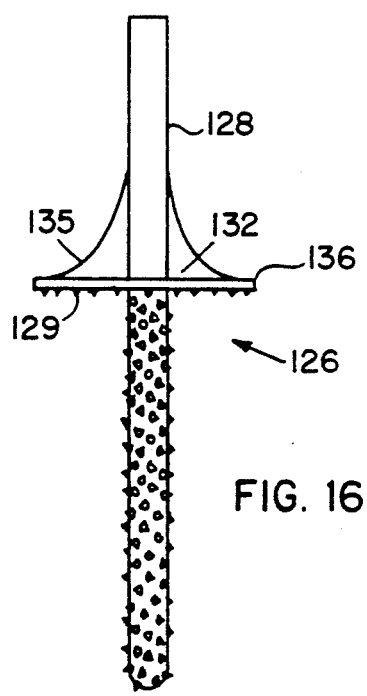
FIG. 16 is a side view of an alternative post of this invention.

Referring to FIG. 16, a side view of an alternate post of this invention is shown. Post 126 has a stem section 128 with a disk 136 and supports 135. There may be as few as one support and as many as sixteen supports though more are possible. The bottom of disk 136 is a cutting surface with projections 129 as occur on the bottom section 130 of post 126. Projections 129 may be as few as one and as many as several hundred. When rotating and depressing the post the projections 129 of disk 136 cut the surface of the root providing anti rotation and providing support against the forces which cause root fracture. The length may be as small as microns and as large as about two millimeters.

Figure 17:
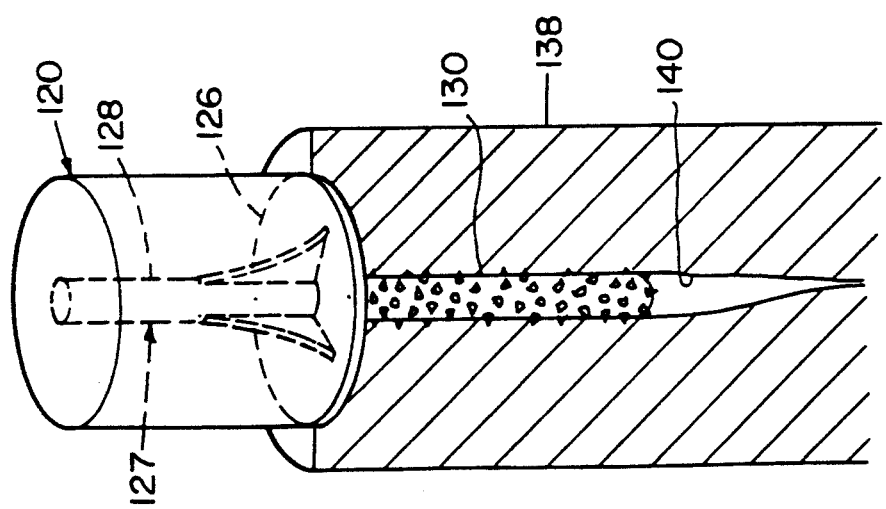
FIG. 17 is an isometric view of the post of FIG. 16 and the core of FIG. 15 assemble in a root stub.

Referring to FIG. 17, an isometric view of the core of FIG. 15 and the post of FIG. 16 assembled in a root stub. Core 120 fits over stem 128 of post 127 such that the disk 126 lies on the top of root stub 138. The bottom section 130 of post 127 fits into root canal space 140.

Figure 18:
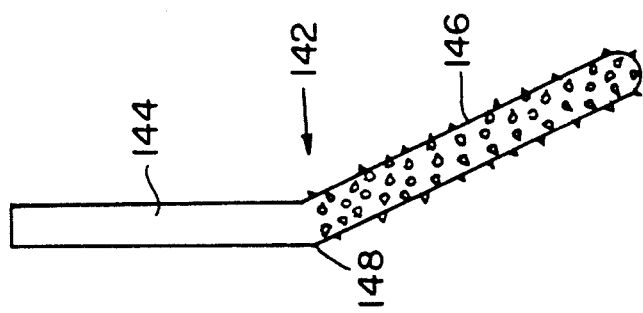
FIG. 18 is a side view of an alternative post of this invention.

Referring to FIG. 18, a side view of an alternate post of this invention is shown. Post 142 has a stem section 144 which is at an angle 148 relative to the bottom section 146.

Figure 19:
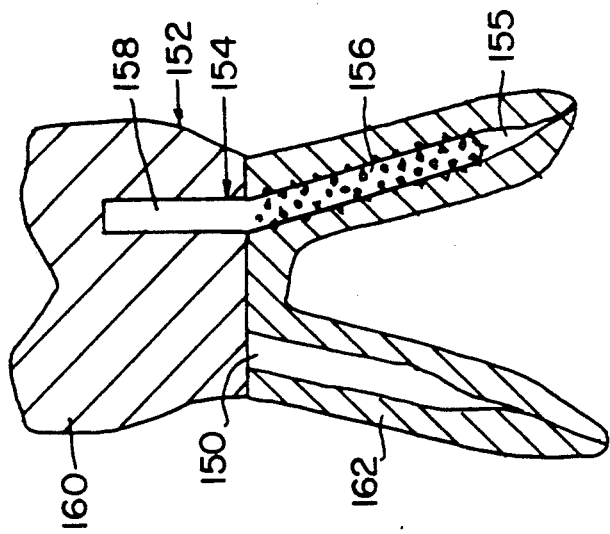
FIG. 19 is a side view of the post of FIG. 18 in a molar tooth.

Referring to FIG. 19, a cross section side view is shown of the post of FIG. 18 in a molar tooth. Post 154 has a bottom section 156 which fits into root canal 155 such that the stem section which is bent remains in the chamber of tooth crown 152. The angled post allows for ease of placement and helps avoid collision of multiple posts at various angles in multiple canals.

Figure 20:
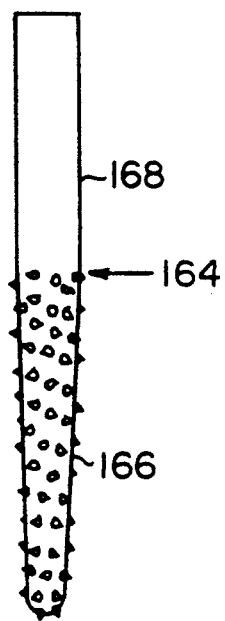
FIG. 20 is a side view of an alternative post of this invention

Referring to FIG. 20, a side view of an alternative post of this invention is shown. Post 164 has stem section 186 and a tapering bottom section 166.

Figure 21:
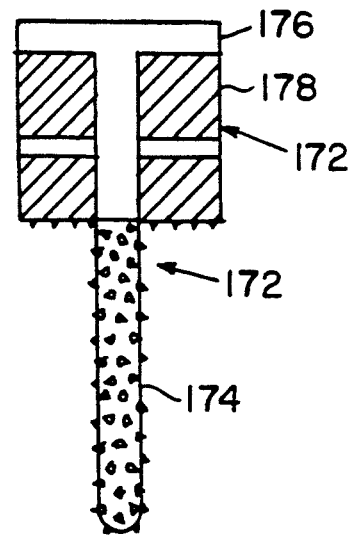
FIG. 21 is a side view of an alternative post of this invention.

Referring to FIG. 21, a side view of an alternative post of this invention is shown. Post 170 has a core 172 which is part of post 170 and attached to bottom section 174. Core section 172 may have metal projections 176 which support other material 178 or be solid metal.

Figure 22:
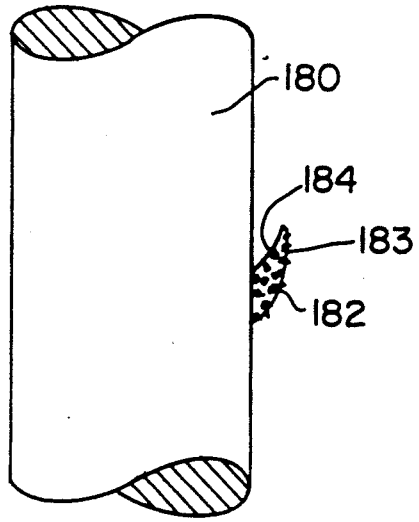
FIG. 22 is a side view of an alternative projection of this invention

Referring to FIG. 22, a side view of an alternative projection of this invention is shown. Projection 183 is attached to post 180 and has a cutting surface 182 and a non cutting surface 184 which join together in an upward direction to form a point which locks into the root when removal is attempted.

Figure 23:
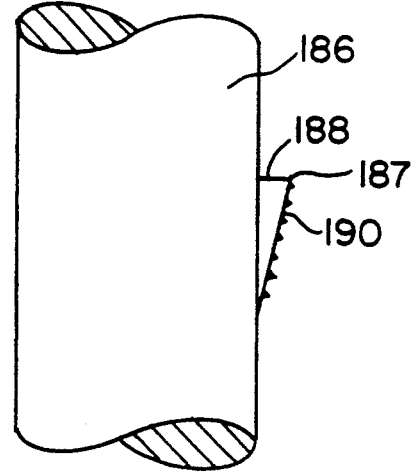
FIG. 23 is a side view of an alternative projection of this invention.

Referring to FIG. 23, a side view of an alternative projection of this invention is shown. Post 186 has projection 187 attached with cutting surface 190 and non cutting area 188 which prevents removal when fully seated and rotated.

I claim:

1. A dental post for insertion into a tooth bore having walls which comprises:
   a stem section having means for attaching a dental prosthesis,
   a bottom section attached to said stem section having a plurality of randomly positioned cutting projections extending outwardly from a surface of said bottom section, whereby when the post is inserted in a tooth bore, said projections extend into said walls.

2. The dental post of claim 1 wherein a disk is attached to a stem.

3. The dental post of claim 2 wherein said disk has a bottom surface and said bottom surface has at least one of said cutting projections extending therefrom.

4. The dental post of claim 2 wherein said disk has a bottom surface with a plurality of said cutting projections.

5. The dental post of any one of claims 3 or 4 including at least one support secured to said disk and said stem.

6. The dental post of claim 5 wherein said disk has at least one hole for pin placement and venting of cement or bonding material.

7. The dental post of any one of claims 3 or 4 wherein said disk has at least one hole for pin placement and venting of bonding.

8. The dental post of any one of claim 1, 2, 3 or 4 wherein said stem is angled in relation to said bottom section.

9. The dental post of any one of claims 1, 2, 3 or 4 wherein said post bottom section has at least one through slot.

10. The dental post of any one of claims 1, 2, 3 or 4 wherein said post bottom section has a plurality of through slots.

11. The dental post of any one of claims 1, 2, 3 or 4 wherein said post bottom section has at least one non-cutting area within said cutting areas of said projections.

12. The dental post of any one of claims 1, 2, 3 or 4 wherein said post bottom section has aa plurality of non-cutting areas within said cutting areas of said projections.

13. The dental post of any one of claims 1, 2, 3 or 4 wherein said post bottom section cutting areas of projections and a non-cutting area at the end of said post.

14. The dental post of any one of claims 1, 2, 3 or 4 wherein said stem has a handle attached.

15. The dental post of any one of claims 1, 2, 3 or 4 wherein said stem has a break off area.

16. The dental post of any one of claims 1, 2, 3 or 4 wherein said bottom section has at least one cement venting groove.

17. The dental post of any one of claims 1, 2, 3 or 4 wherein said bottom section has a plurality of cement venting grooves.

18. The dental post of any one of claims 1, 2, 3 or 4 wherein said stem is an attached core.

19. The dental post of any one of claims 1, 2, 3 or 4 wherein a matching core fits over said stem.

20. The dental post of claim 2 including at least one support secured to said disk and said stem.

21. The dental post of claim 2 wherein said disk has at least one hole for pin placement and venting of cement or bonding material.

* * * * *